US012357222B2

(12) United States Patent
Saisho et al.

(10) Patent No.: US 12,357,222 B2
(45) Date of Patent: Jul. 15, 2025

(54) ELECTROMYOGRAPHY PROCESSING APPARATUS, ELECTROMYOGRAPHY PROCESSING METHOD AND ELECTROMYOGRAPHY PROCESSING PROGRAM

(71) Applicant: Nippon Telegraph and Telephone Corporation, Tokyo (JP)

(72) Inventors: Osamu Saisho, Musashino (JP); Shingo Tsukada, Musashino (JP); Hiroshi Imamura, Musashino (JP); Atsunori Mihara, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 869 days.

(21) Appl. No.: 17/623,448

(22) PCT Filed: Jun. 28, 2019

(86) PCT No.: PCT/JP2019/025796
§ 371 (c)(1),
(2) Date: Dec. 28, 2021

(87) PCT Pub. No.: WO2020/261528
PCT Pub. Date: Dec. 30, 2020

(65) Prior Publication Data
US 2022/0346696 A1    Nov. 3, 2022

(51) Int. Cl.
*A61B 5/397* (2021.01)
*A61B 5/00* (2006.01)
(52) U.S. Cl.
CPC ............ *A61B 5/397* (2021.01); *A61B 5/7242* (2013.01); *A61B 5/7264* (2013.01); *A61B 5/7275* (2013.01)

(58) Field of Classification Search
CPC ..... A61B 5/397; A61B 5/7242; A61B 5/7264; A61B 5/7275
(Continued)

(56) References Cited

U.S. PATENT DOCUMENTS

| 10,206,598 B2* | 2/2019 | Bounyong | ............ A61B 5/389 |
| 2016/0157743 A1* | 6/2016 | Bounyong | ............ A61B 5/389 |
| | | | 600/301 |
| 2018/0256079 A1* | 9/2018 | Yang | .................... A61B 5/1107 |

FOREIGN PATENT DOCUMENTS

| CN | 102319482 A * | 1/2012 | |
| TW | 1631934 B * | 8/2018 | ........... A61B 5/1118 |
| WO | WO-2017073694 A1 * | 5/2017 | ........... A61B 5/0476 |

OTHER PUBLICATIONS

Journal of Electromyography and Kinesiology, "Intra-session repeatability of lower limb muscles activation pattern during pedaling", Dorel, Sylvain et al., Oct. 2008, vol. 18, No. 5, pp. 857-865, ISSN: 1050-6411, DOI: 10.1016/j.jelekin.2007.03.002 (Year: 2008 ).*

(Continued)

*Primary Examiner* — Stephanie E Bloss
*Assistant Examiner* — Kevin C Butler
(74) *Attorney, Agent, or Firm* — Fish & Richardson P.C.

(57) ABSTRACT

An electromyography processing apparatus includes an electromyography acquiring unit configured to generate electromyography data indicating the time course of an electromyography acquired from an electrode set on a predetermined muscle of an exerciser performing a repetitive exercise, and an evaluation unit configured to calculate and output a reproducibility index indicating the reproducibility of the repetitive exercise from the reproducibility of a transition of the electromyography in the repetitive exercise.

7 Claims, 15 Drawing Sheets

(58) Field of Classification Search
USPC .................................................... 73/379.01
See application file for complete search history.

(56) References Cited

OTHER PUBLICATIONS

Dorel et al., "Intra-session repeatability of lower limb muscles activation pattern during pedaling," Journal of Electromyography and Kinesiology, Oct. 2008, 18(5):857-865.
Mochida, "Sports performance improvement system based on brain science," Sensory and Motor Research Group, Human Information Science Laboratory, 2016, 2 pages (Abstract with English translation).

* cited by examiner

| ONSET IDENTIFIER | START TIME | END TIME |
|---|---|---|
| | ↖ 13 ONSET DATA | |
| 1 | ..... | ..... |
| 2 | ..... | ..... |
| ..... | ..... | ..... |

ELECTROMYOGRAPHY PROCESSING APPARATUS, ELECTROMYOGRAPHY PROCESSING METHOD AND ELECTROMYOGRAPHY PROCESSING PROGRAM

CROSS-REFERENCE TO RELATED APPLICATIONS

This application is a National Stage application under 35 U.S.C. § 371 of International Application No. PCT/JP2019/025796, having an International Filing Date of Jun. 28, 2019, the disclosure of which is considered part of the disclosure of this application, and is incorporated in its entirety into this application.

TECHNICAL FIELD

The present disclosure relates to an electromyography processing apparatus, an electromyography processing method, and an electromyography processing program.

BACKGROUND ART

Electromyography is physiological information that directly represents how to use the body, and in order to improve various sports skills, the utilization of electromyography has attracted attention. Electromyography is a voltage that occurs when a muscle is moved. Electromyography is also referred to as electromyography (EMG). The amplitude of electromyography increases when strength is applied, and approaches 0 when strength is lost. It is expected that by focusing on electromyography, an exerciser himself/herself will be able to interpret whether the muscles are properly used at a training site and apply this to the training to improve his/her performance.

However, electromyography is only an electrical signal, and thus it is difficult to interpret electromyography data, and there is a need for a technique for processing electromyography data such that an exerciser himself/herself can understand the electromyography data. For example, there is a technique in which, for a plurality of muscles, the timing at which a muscle moves and electromyography increases is detected and a sound at a frequency applied to each muscle is generated to provide feedback to an exerciser by means of the sound (see NPL 1).

CITATION LIST

Non Patent Literature

NPL 1: NTT Communication Science Laboratories, "Open House 2016, Shaping the Athletic Brain!", [online], 2016, NTT, [Searched on Sep. 25, 2018]; Internet (URL: http://www.kecl.ntt.co.jp/openhouse/2016/exhibition/28/index-.html)

SUMMARY OF THE INVENTION

Technical Problem

Exercise such as running or pedaling a bike is a repetitive exercise that repeats an identical motion. In a repetitive exercise, stability or reproducibility at which the same motion is repeated is important. For example, there is a method in which a power meter is mounted on a bike pedal to confirm that an identical motion is repeated by the transition of strength applied to the pedal. However, this method cannot identify a factor due to which the identical motion cannot be repeated. There is no method for evaluating the stability of movement of each muscle in a repetitive exercise.

The present disclosure has been made in view of the above circumstances, and an object of the present disclosure is to provide a technique for evaluating the stability of movement of each muscle in a repetitive exercise.

Means for Solving the Problem

A electromyography processing apparatus according to one aspect of the present disclosure includes an electromyography acquiring unit configured to generate electromyography data indicating a time course of an electromyography acquired from an electrode set on a predetermined muscle of an exerciser performing repetitive exercises, and an evaluation unit configured to calculate and output a reproducibility index indicating a reproducibility of each of the repetitive exercises from a reproducibility of a transition of the electromyography in each of the repetitive exercises.

A electromyography processing method according to one aspect of the present disclosure includes generating, by a computer, electromyography data indicating a time course of an electromyography acquired from an electrode set on a predetermined muscle of an exerciser performing repetitive exercises, and calculating and outputting, by the computer, a reproducibility index indicating a reproducibility of each of the repetitive exercises from a reproducibility of a transition of the electromyography in each of the repetitive exercises.

An aspect of the present disclosure is an electromyography processing program causing a computer to operate as the electromyography processing apparatus.

Effects of the Invention

According to the present disclosure, a technique for evaluating the stability of movement of each muscle in a repetitive exercise can be provided.

BRIEF DESCRIPTION OF DRAWINGS

FIG. 3 is a diagram for explaining an example of a data structure for onset data.

DESCRIPTION OF EMBODIMENTS

Hereinafter, an embodiment of the present disclosure will be described with reference to the drawings. Note that in descriptions of the drawings, the same components are denoted by the same reference signs and explanations thereof will be omitted.

An electromyography processing apparatus 1 according to the embodiment of the present disclosure will be described with reference to FIG. 1. The electromyography processing apparatus 1 outputs data with which an exerciser performing an exercise such as a cycling competition or running in which repetitions are repeated can grasp changes in muscle movement during the repetitive exercise.

Figure 2:
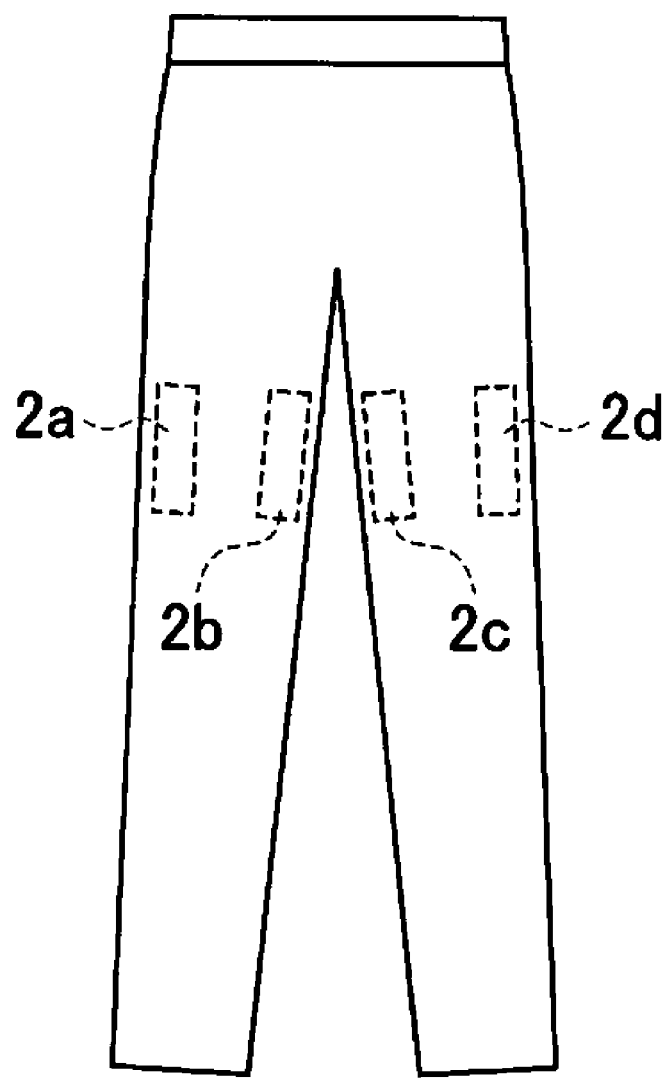
FIG. 2 is a diagram for explaining an example of tights in which electrodes are provided.

On the inside of an item of clothing worn by the exerciser, electrodes 2a to 2d are provided as illustrated in FIG. 2, and the electrodes 2a to 2d come into contact with the skin of the exerciser. The electromyography processing apparatus 1 acquires, via the electrodes 2a to 2d, electromyographies of muscles located subcutaneously at the locations where the electrodes are provided. The electrodes 2a to 2d may be attached to the skin of the exerciser.

In the embodiment of the present disclosure, the electrodes are provided on pairs of left and right muscles. In the example illustrated in FIG. 2, the electrodes 2a and 2d acquire electromyographies of the left and right vastus lateralis muscles, respectively. The electrodes 2b and 2c acquire electromyographies of the left and right biceps femoris muscles (hamstrings), respectively. During the exercise by the exerciser, the electromyography processing apparatus 1 sequentially acquires electromyographies obtained from the electrodes, analyzes the acquired electromyographies, and outputs the result of the analysis. Note that when it is not particularly necessary to differentiate between the electrodes 2a to 2d, they may be referred to as the electrodes 2. Note that the positions and the number of the electrodes 2 illustrated in FIG. 2 are exemplary and without limitation. The electrodes 2 are provided at positions at which it is possible to acquire the electromyography of a muscle set to be measured, as appropriate.

Figure 1:
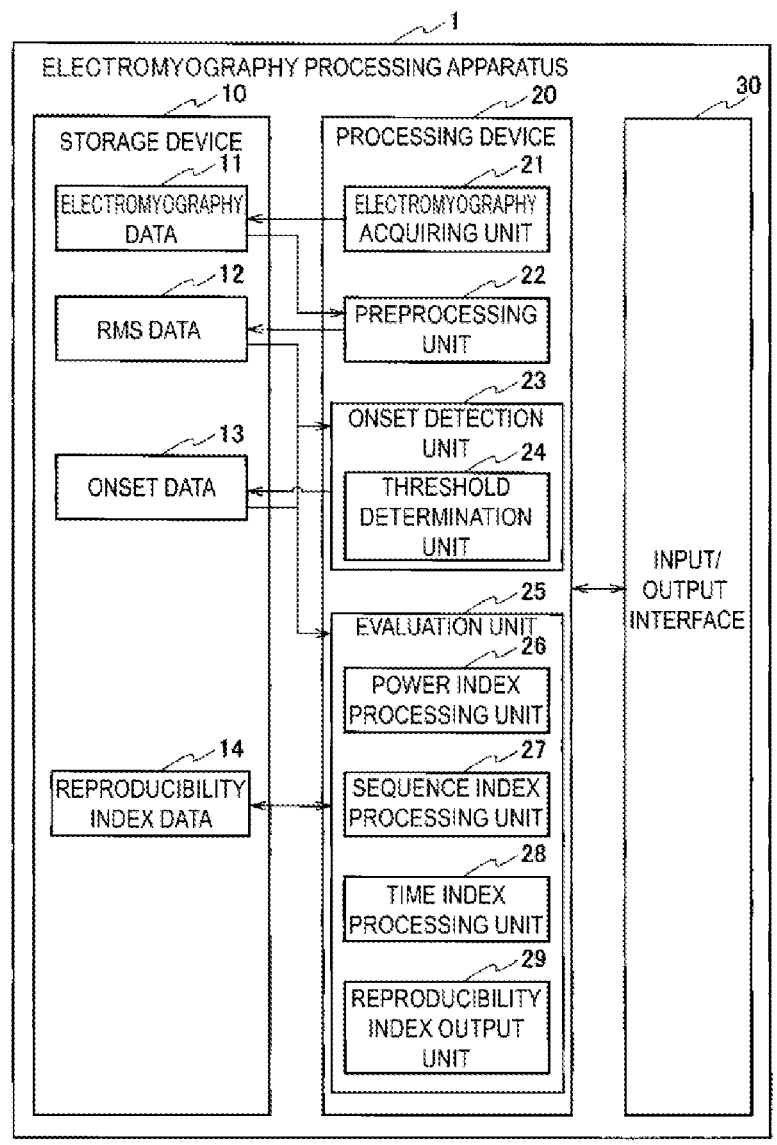
FIG. 1 is a diagram for explaining functional blocks of an electromyography processing apparatus according to an embodiment of the present disclosure.

As illustrated in FIG. 1, the electromyography processing apparatus 1 according to the embodiment of the present disclosure includes a storage device 10 and a processing device 20.

The storage device 10 stores an electromyography processing program and stores electromyography data 11, RMS data 12, onset data 13, and reproducibility index data 14.

The electromyography data 11 is data indicating the time course of an electromyography acquired from an electrode 2 set on a predetermined muscle of an exerciser performing a repetitive exercise. The electromyography data 11 is data in which a value of the electromyography obtained from the electrodes 2 is associated with the time at which the value is acquired. When electromyographies are acquired from a plurality of muscles, the electromyography data 11 is generated for each muscle.

The RMS data 12 includes a root-mean-square (RMS) value of electromyograpies for each predetermined time.

The RMS data 12 is data in which a calculated RMS value of electromyographies is associated with a time corresponding to the RMS value. When the electromyography data 11 includes electromyographies of a plurality of muscles, the RMS data 12 is generated for each muscle.

The onset data 13 identifies a section (onset section) of the electromyography data 11, in which the electromyography has increased. As illustrated in FIG. 3, for example, the onset data 13 is data in which an onset identifier identifying an onset section is associated with a start time and an end time of the onset section. When the electromyography data 11 is generated for each of a plurality of muscles, the onset data 13 is generated for each of the plurality of muscle.

The reproducibility index data 14 includes a reproducibility index calculated for each predetermined time. The reproducibility index data 14 is data in which a calculated reproducibility index is associated with an identifier of a time corresponding to the reproducibility index. In the embodiment of the present disclosure, the reproducibility index is a power index, a sequence index, or a time index. The reproducibility index may be an index in which two or more indexes of the power index, the sequence index, and the time index are integrated.

The processing device 20 includes an electromyography acquiring unit 21, a preprocessing unit 22, an onset detection unit 23, and an evaluation unit 25.

The electromyography acquiring unit 21 generates the electromyography data 11 indicating the time course of an electromyography acquired from an electrode 2 set on a predetermined muscle of an exerciser performing a repetitive exercise. When electromyographies are acquired from a plurality of electrodes, the electromyography acquiring unit 21 generates the electromyography data 11 for each muscle corresponding to each electrode.

The preprocessing unit 22 removes noise from an electromyography value of the electromyography data 11 and calculates an RMS value on the basis of the electromyography value after noise removal to generate the RMS data 12. The preprocessing unit 22 calculates an RMS value of the electromyography data 11 for each predetermined time to generate root-mean-square data (RMS data 12) including an RMS value for each time. When the electromyographies of a plurality of muscles are acquired, the preprocessing unit 22 generates the RMS data 12 for each of the plurality of muscles.

Figure 4:
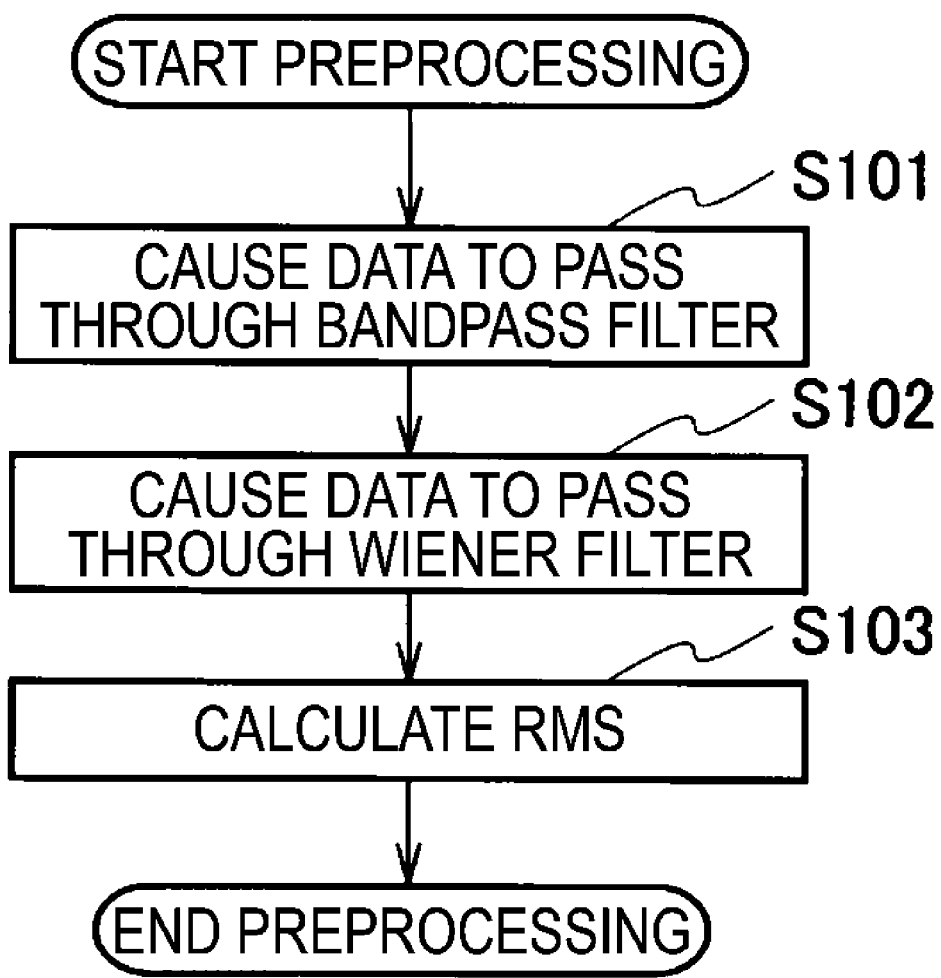
FIG. 4 is a flowchart for explaining preprocessing by a preprocessing unit.

Preprocessing by the preprocessing unit 22 will be described with reference to FIG. 4.

First, in step S101, the preprocessing unit 22 causes the electromyography data 11 to pass through a bandpass filter. In step S102, the preprocessing unit 22 causes the data that has passed through the bandpass filter in step S101 to pass through a Wiener filter.

In step S103, the preprocessing unit 22 calculates a root-mean-square for the data that has passed through the Wiener filter in step S102 to generate the RMS data 12.

The preprocessing unit 22 causes the electromyography data 11 to pass through the bandpass filter to filter out frequencies other than the frequency of an electromyography. The electromyography data 11 including a electromyography acquired from the electrodes 2 includes various noise such as noise generated by a body movement called a "motion artifact", and noise generated by electricity or the like occurring in the skin even without movement. When the electromyography data 11 passes through the bandpass filter, noise outside the frequency band of an electromyography is removed. As a result, the electromyography data 11 can be narrowed into the frequency band of the electromyography to be acquired.

The frequency of the bandpass filter is set in accordance with the noise included in the electromyography data 11. The preprocessing unit 22 is not limited to a bandpass filter that defines an upper limit value and a lower limit value, and a high-pass filter or a low-pass filter may be used which does not define either the upper limit or the lower limit. The upper limit value and the lower limit value of the bandpass filter are determined on the basis of a sampling frequency of the electromyography to be acquired or a characteristic of a device. For example, in a case where the sampling frequency is 500 Hz, the upper limit value is set to 249 Hz on the basis of a sampling theorem, and the lower limit is set to 10 Hz from a main frequency characteristic of the electromyography. As a frequency filtering method, for example, a Butterworth filter is common, but the frequency filtering method is not limited thereto.

The preprocessing unit 22 applies the Wiener filter to the data that has passed through the bandpass filter to remove noise on the entire electromyography data 11, thereby removing signals (noise) other than an electrical signal generated by muscle activation. When data has been acquired for measuring noise intensity, the intensity of noise removal by the Wiener filter is determined on the basis of the data. When the noise intensity has not been measured, the intensity of noise removal is determined on the basis of the electromyography data 11. The preprocessing unit 22 determines the intensity of noise removal on the basis of, for example, electromyographies of all sections (each time) of the electromyography data 11. Alternatively, the preprocessing unit 22 may identify an onset section by processing equivalent to that performed by the onset detection unit 23 described below on the basis of the electromyography data 11 or the data that has passed through the bandpass filter, and determine the intensity of noise removal on the basis of an electromyography of a section that is not the onset section.

Figure 5:
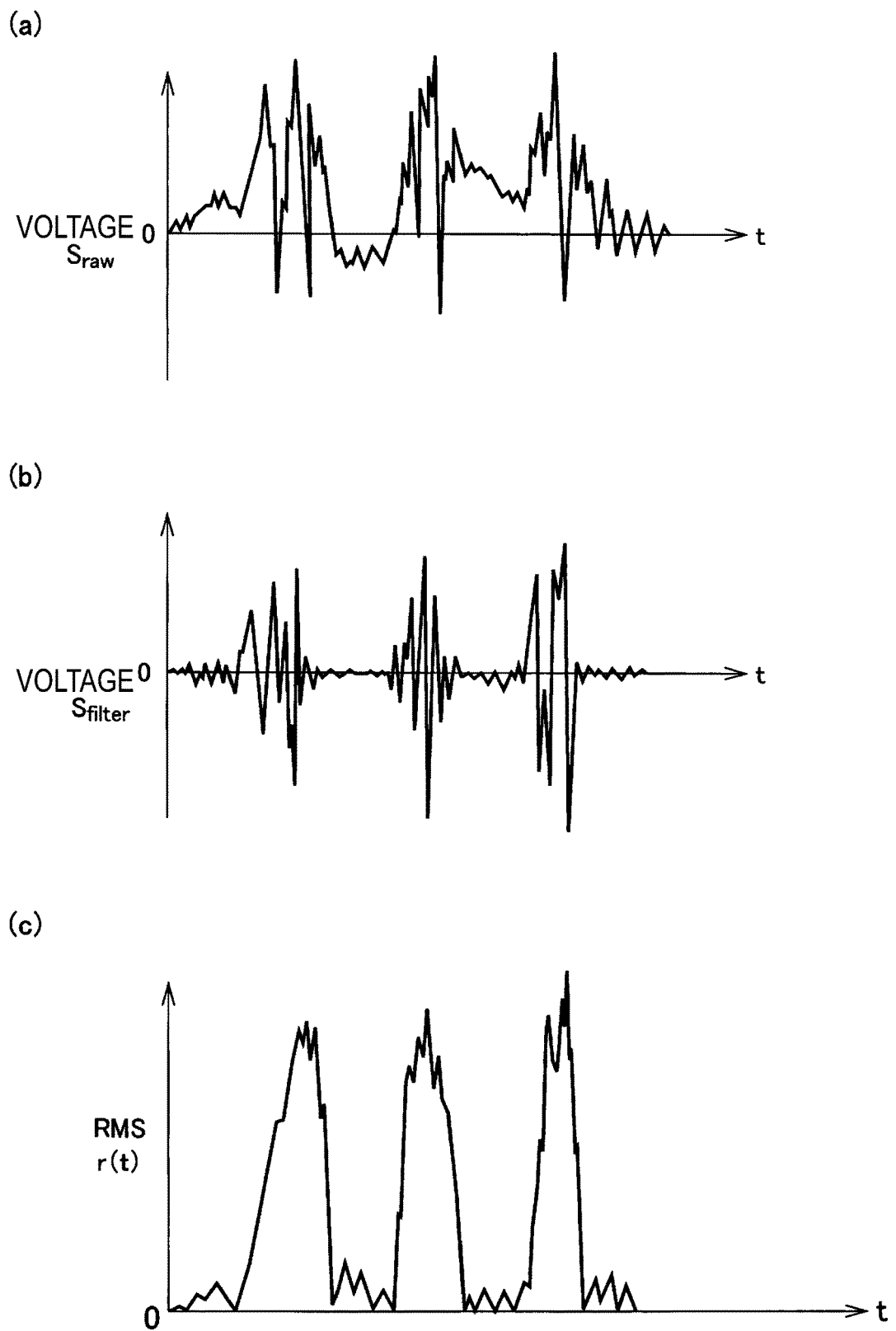
FIG. 5 shows an example of signal input and output by the preprocessing unit.

When the preprocessing unit 22 applies the bandpass filter and the Wiener filter to the electromyography data 11 shown in FIG. 5(a) to remove noise, the data shown in FIG. 5(b) is obtained. In the data shown in FIG. 5(b), it is easier to distinguish between a section in which the voltage is close to 0 and a section in which the voltage is not 0, than in the data shown in FIG. 5(a).

Figure 6:
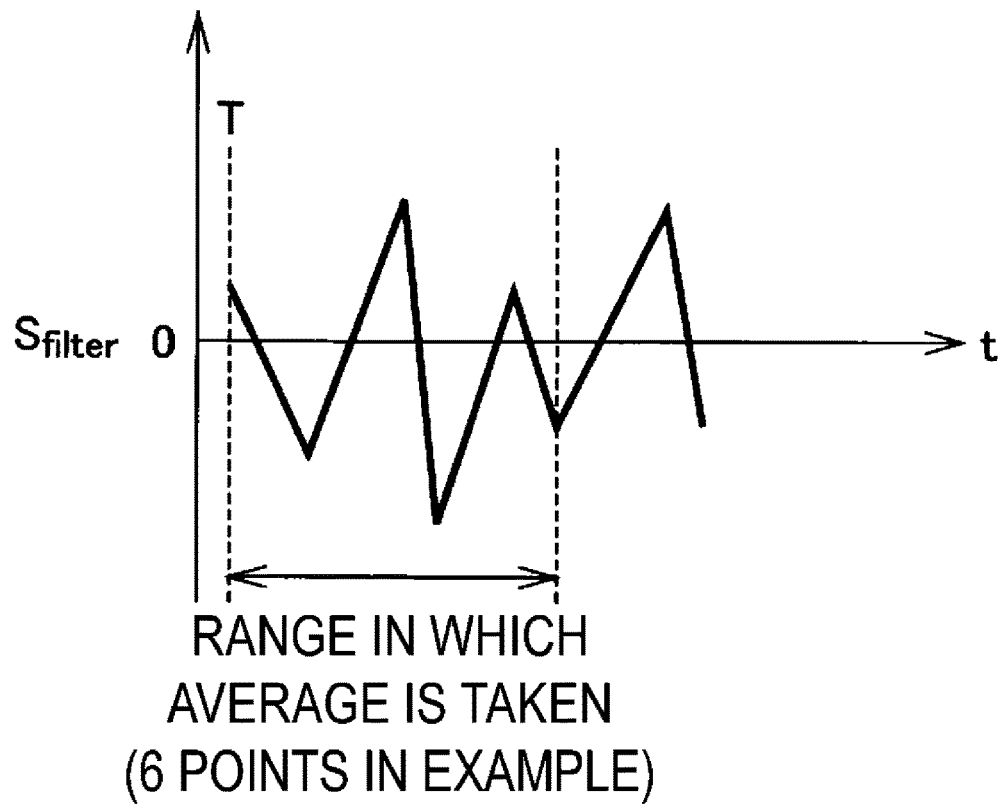
FIG. 6 is a diagram for explaining a root-mean-square calculated by the preprocessing unit.

In addition, the preprocessing unit 22 calculates a root-mean-square on the data that has passed through the bandpass filter and the Wiener filter. As shown in FIG. 6(a), the preprocessing unit 22 calculates r(T), which is the RMS value, by the equation shown in FIG. 6(b) on data in a range for which an average is taken, out of the data that has passed through the filters. The preprocessing unit 22 repeats the processing of calculating a root-mean-square for each section to generate the RMS data 12.

As a result, the preprocessing unit 22 obtains the data shown in FIG. 5(c). Compared to FIG. 5(b), the signal shown in FIG. 5(c) can express the output of the electromyography in a single motion as one unit.

The onset detection unit 23 detects an onset section in which the electromyography has increased due to repetitive exercise by the exerciser, in the electromyography data 11. The onset detection unit 23 refers to the RMS data 12 obtained by processing such as noise removal from the electromyography data 11, and identifies a section in a time axis in which the output of the electromyography is equal to or greater than a predetermined threshold as the onset section, to output the onset data 13. The onset detection unit 23 sets a sliding window for onset detection for a predetermined time of the RMS data 12, and determines that the predetermined time is an onset portion when the average of the RMS values in the sliding window is higher than a threshold. The onset detection unit 23 identifies a section in which the onset portion is continuous as the onset section and outputs the onset data 13. The onset section detected by the onset detection unit 23 is processed by the evaluation unit 25 described below.

The onset detection unit 23 includes a threshold determination unit 24. The threshold determination unit 24 determines a threshold for detecting the onset section. The threshold determined by the threshold determination unit 24 is a static threshold or a dynamic threshold.

The static threshold is a fixed value used to detect the onset section in all sections of a measurement time for the repetitive exercise. When determining the static threshold, the threshold determination unit 24 uses, for example, a threshold-based method (Hodges, P. and Bui, B, A comparison of computer-based methods for the determination of onset of muscle contraction using electromyography, Electroencephalogr' Clin' Neurophysiol', 101 (1996), 511-519) to determine the static threshold on the basis of electromyography data measured at rest in advance. The static threshold is applied at each time of the RMS data 12 and is suitable for a measurement under a static environment for a short period of time, such as in a laboratory.

The dynamic threshold is a variable value that is calculated each time the onset section is determined. When determining the dynamic threshold, for the time at which the onset is detected, the threshold determination unit 24 sets a sliding window for threshold detection that is longer than the time of the sliding window for onset detection, and determines a threshold on the basis of an average of the RMS values in the sliding window for threshold detection.

When the sliding window for onset detection slides, the sliding window for threshold detection also slides. Each time the sliding window for onset detection moves, the sliding window for threshold detection may move. Alternatively, the sliding window for threshold detection may slide less frequently than the sliding window for onset detection. In the onset detection, it is sufficient to use the threshold calculated most recently.

When the threshold is dynamically determined, it is possible to determine the threshold depending on noise included in the electromyography measured by the electrodes 2 due to a status change such as sweating or displacement of an electrode in a repetitive exercise. It is possible to determine noise in response to a change in measurement value due to a change in the state of the skin or an electrode, a change in the magnitude of the muscle output, and the like in measurement performed for a long period of time during a repetitive exercise, and thus it is possible to appropriately remove the noise.

Onset detection processing by the onset detection unit 23 will be described with reference to FIG. 7.

Figure 8:
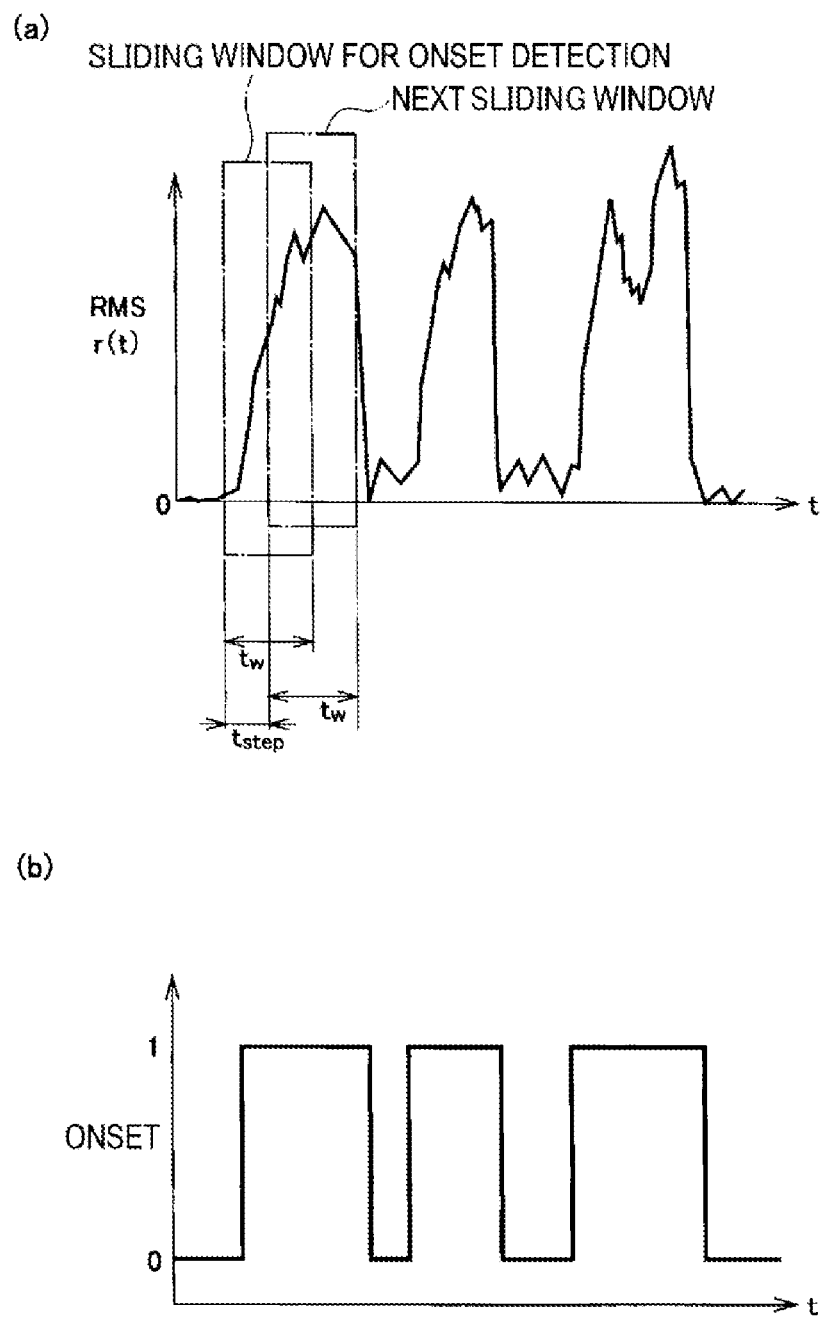
FIG. 8 is a diagram for explaining a sliding window for onset detection and an onset section.

In step S201, the onset detection unit 23 sets a sliding window that slides in the time axis. For example, as shown in FIG. 8(a), a sliding window for onset detection is set in the time axis. The time width of the sliding window for onset detection is $t_w$.

In step S202, the onset detection unit 23 determines a threshold for identifying the onset section by the threshold determination unit 24. The threshold determined here is a static threshold or a dynamic threshold. The onset detection unit 23 causes the threshold determination unit 24 to determine a threshold specified by an operator or the like in advance.

In step S203, the onset detection unit 23 determines whether the average of the RMS values in the sliding window set in step S201 is greater than the threshold determined in step S202. When the average is greater than the threshold, the onset detection unit 23 sets the inside of the sliding window as the onset portion in step S204, and when the average is smaller than the threshold, the onset detection unit 23 sets the inside of the sliding window as an offset portion in step S205.

In step S206, the onset detection unit 23 determines whether the sliding window has covered all times of the RMS data 12 and the determination has ended for all sections. When the determination has not ended for all sections, the sliding window is slided in step S201 to perform the processing of step S202 to step S205 on the basis of the sliding window after sliding. For example, as shown in FIG. 8(b), the sliding window is shifted by $t_{step}$ to set the next sliding window. The time width of the next sliding window is $t_w$, similar to the sliding window for onset detection. For example, the window width of the sliding window for detecting the onset section is 0.2 seconds and the window width of the sliding window for detecting the onset section is 0.1 seconds.

When the determination has ended for all sections, the onset detection unit 23 consolidates the continuous onset portions as one onset section to identify each onset section in step S207. When a time detected as the onset portion in step S204 continues from a time detected as another onset portion, the onset detection unit 23 sets the continuous onset portions as one onset section. As a result, as shown in FIG. 8(b), it is possible to identify a plurality of onset sections in the measurement time for the repetitive exercise. The onset detection unit 23 identifies a start time and an end time for each onset section to generate the onset data 13.

Figure 7:
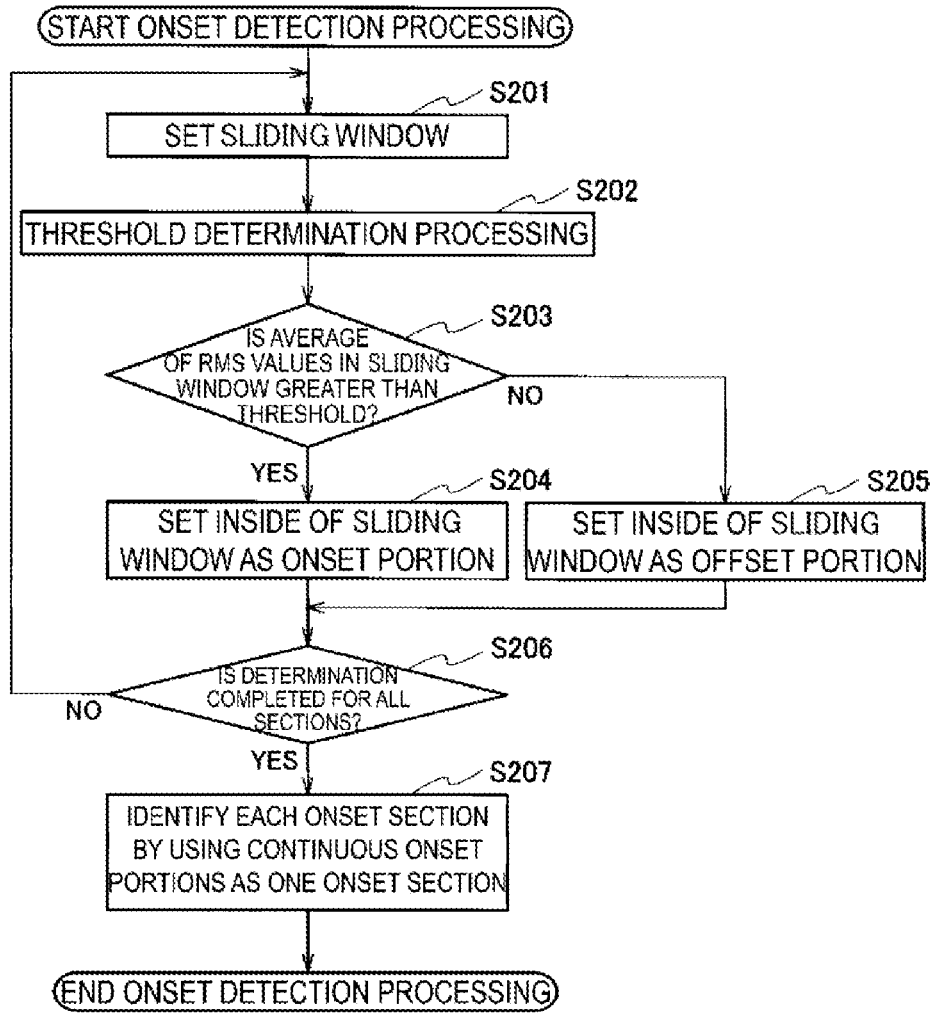
FIG. 7 is a flowchart for explaining onset detection processing by an onset detection unit.

Note that the processing illustrated in FIG. 7 is exemplary and without limitation. When the window width of the sliding window for detecting the onset section is 0.2 seconds and the window width of the sliding window for detecting the onset section is 0.1 seconds, the determination of whether a predetermined section is an onset section is repeated twice. In this case, when the predetermined section is determined as being an onset section in any of the determinations, the predetermined section may be determined as being an onset section. Alternatively, when the predetermined section is determined as being an onset section in both of the two determinations, the predetermined section may be determined as being an onset section or otherwise determined as not being an onset section. Also, in a case where the determination of whether the predetermined section is an onset section is repeated three times or more, similarly, the determination may be made on the basis of a plurality of determination results for the predetermined section.

Evaluation Unit

The evaluation unit 25 refers to the RMS data 12, and calculates and outputs an index that quantifies the exercise performed by the exerciser. The evaluation unit 25 calculates a reproducibility index indicating the reproducibility of the repetitive exercise from the reproducibility of the transition of the electromyography in the repetitive exercise, and outputs the reproducibility index.

The evaluation unit 25 includes a power index processing unit 26, a sequence index processing unit 27, a time index processing unit 28, and a reproducibility index output unit 29.

The power index processing unit 26 calculates a power index. The power index becomes good when there is no change in power in the repetitive exercise.

The sequence index processing unit 27 calculates a sequence index. The sequence index becomes good when reproducibility is high for a sequence of times in which a predetermined condition is satisfied in the repetitive exercise.

The time index processing unit 28 calculates a time index. The time index becomes good when reproducibility is high for a time in which a predetermined condition is satisfied in the repetitive exercise.

The reproducibility index output unit 29 outputs a reproducibility index. The reproducibility index is calculated from any one or more of the power index, the sequence index, and the time index. The reproducibility index may be any one of the power index, the sequence index, and the time index, or may be an index in which two or more of these are integrated.

Power Index Processing Unit

The power index processing unit 26 calculates the power index from the variance of integrated values of the electromyographies for each predetermined time.

First, the power index processing unit 26 normalizes the RMS data 12. The RMS data 12 includes the RMS value of the electromyographies for each predetermined time. The electromyography varies greatly depending on the manner of sweating, the position of the electrodes with respect to the muscles, the intensity of the exercise, and the like. The power index processing unit 26 uses the RMS value in the sliding window to calculate the normalized values in order to suppress effects caused by the manner of sweating, the positions of the electrodes with respect to the muscles, the intensity of the exercise, and the like. The window width of the sliding window is a time a, which can be recognized as one block of the exercise. In the embodiment of the present disclosure, the time a of the window width is 4 seconds. The step width of the sliding window is the predetermined time for which the RMS value is calculated in the RMS data 12.

In the sliding window set in this manner, the RMS value normalized by means of Equation (1) is referred to as a normalized RMS value in the present embodiment of the present disclosure.

[Math. 1]

$$\tilde{r}_t = \frac{r_t - \min_{s \in [t-\frac{a}{2}, t+\frac{a}{2}]} r_s}{\max_{s \in [t-\frac{a}{2}, t+\frac{a}{2}]} r_s - \min_{s \in [t-\frac{a}{2}, t+\frac{a}{2}]} r_s} \qquad \text{Equation (1)}$$

$r_t$ : RMS value at time $t$
$\tilde{r}_t$ : Normalized RMS value at time $t$
$a$ : Window width The normalized RMS value falls within a range of [0, 1]. RMS value normalization is performed for each RMS value of the RMS data 12 acquired from each muscle.

When one muscle is focused on to output the power index, the power index processing unit 26 normalizes the RMS value for the muscle. When a plurality of muscles is focused on to output the power index, the power index processing unit 26 calculates the normalized RMS value for each muscle.

For example, for one muscle, the power index processing unit 26 calculates an integrated value of the RMS value for each onset section of the muscle. The power index processing unit 26 outputs the variance of the integrated values for the onset sections included in the predetermined section as the power index in this section.

When the power index is calculated for a plurality of muscles, the power index processing unit 26 identifies the time of the onset section for one muscle of the plurality of muscles. The power index processing unit 26 calculates an average of the integrated values of the RMS values of the plurality of muscles for the identified time. The power index processing unit 26 outputs the variance of the total of the integrated values for the onset sections included in the predetermined section as the power index in this section.

The predetermined section is, for example, a continuous time that includes a plurality of onset sections, in which it is easy to evaluate the variance calculated for each predetermined section. One onset section corresponds to one cycle of the repetitive exercise. The predetermined section differs depending on the exercise and the exerciser, but 4 to 30 seconds provides an indication.

When the power index is small, specifically, when the variance of the integrated values for the onset sections in the predetermined section is small, this indicates that the exercise is performed with a similar power each time in the repetitive exercise of a plurality of repetitions in the predetermined section, whereby it is evaluated that the reproducibility is high. A small power index is evaluated as indicating a highly reproducible and stable repetitive exercise.

When the power index is large, specifically, when the variance of the integrated values for the onset sections in the predetermined section is large, this indicates that the exercise is performed with a different power each time in the repetitive exercise of a plurality of repetitions in the predetermined section. A large power index is evaluated as indicating a less reproducible and unstable repetitive exercise.

The power index processing unit 26 may calculate, as the power index, a coefficient of variation obtained by dividing the standard deviation of the integrated values of the electromyographies for each predetermined time period by the average of the integrated values. When the coefficient of variation is set as the power index, effects associated with the magnitude of the integrated values can be suppressed, and the power index can be made to be an index indicating the relative variance of the integrated values.

Figure 9:
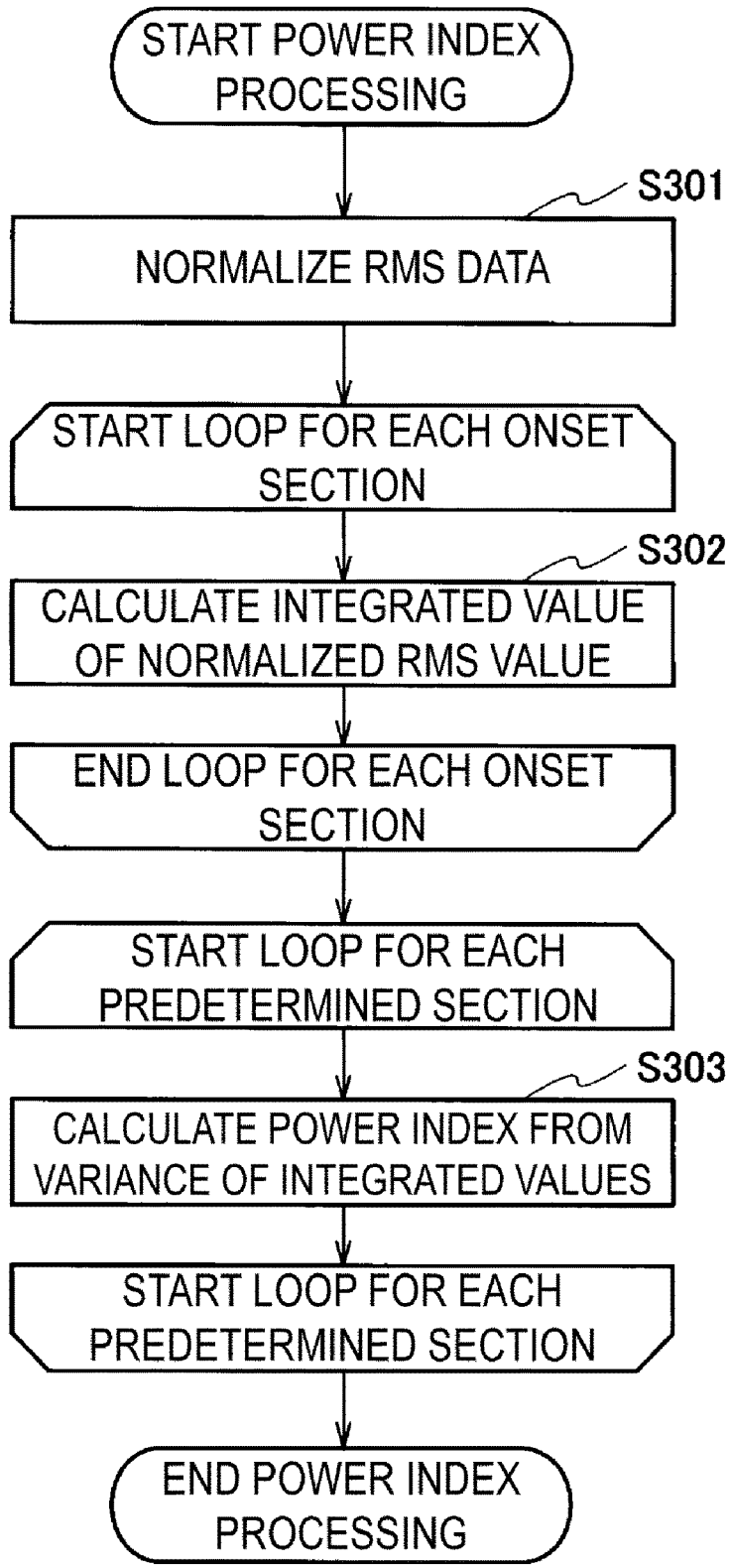
FIG. 9 is a flowchart for explaining power index processing by a power index processing unit.

Power index processing by the power index processing unit 26 will be described with reference to FIG. 9.

First, in step S301, the power index processing unit 26 normalizes the RMS data 12 of each muscle by means of Equation (1).

The power index processing unit 26 performs the processing in step S302 for the onset sections detected by the onset detection unit 23. In step S302, the power index processing unit 26 calculates the integrated value of the RMS value in the onset section to be processed. When the power index is calculated for a plurality of muscles, the power index processing unit 26 calculates integrated values of the RMS values of the muscles for the onset section of one muscle, and calculates an average of the integrated values.

When the processing in step S302 ends for each onset section, the power index processing unit 26 performs processing in step S303 for the predetermined section. The predetermined section is longer than the time of the onset section and is a time that includes a plurality of onset sections. In step S303, the power index processing unit 26 calculates the variance of the integrated values calculated in S302 for the section to be processed. The power index processing unit 26 sets the calculated variance as the power index in the section to be processed. When the power index has been calculated for each section, the power index processing unit 26 ends the processing.

Figure 10:
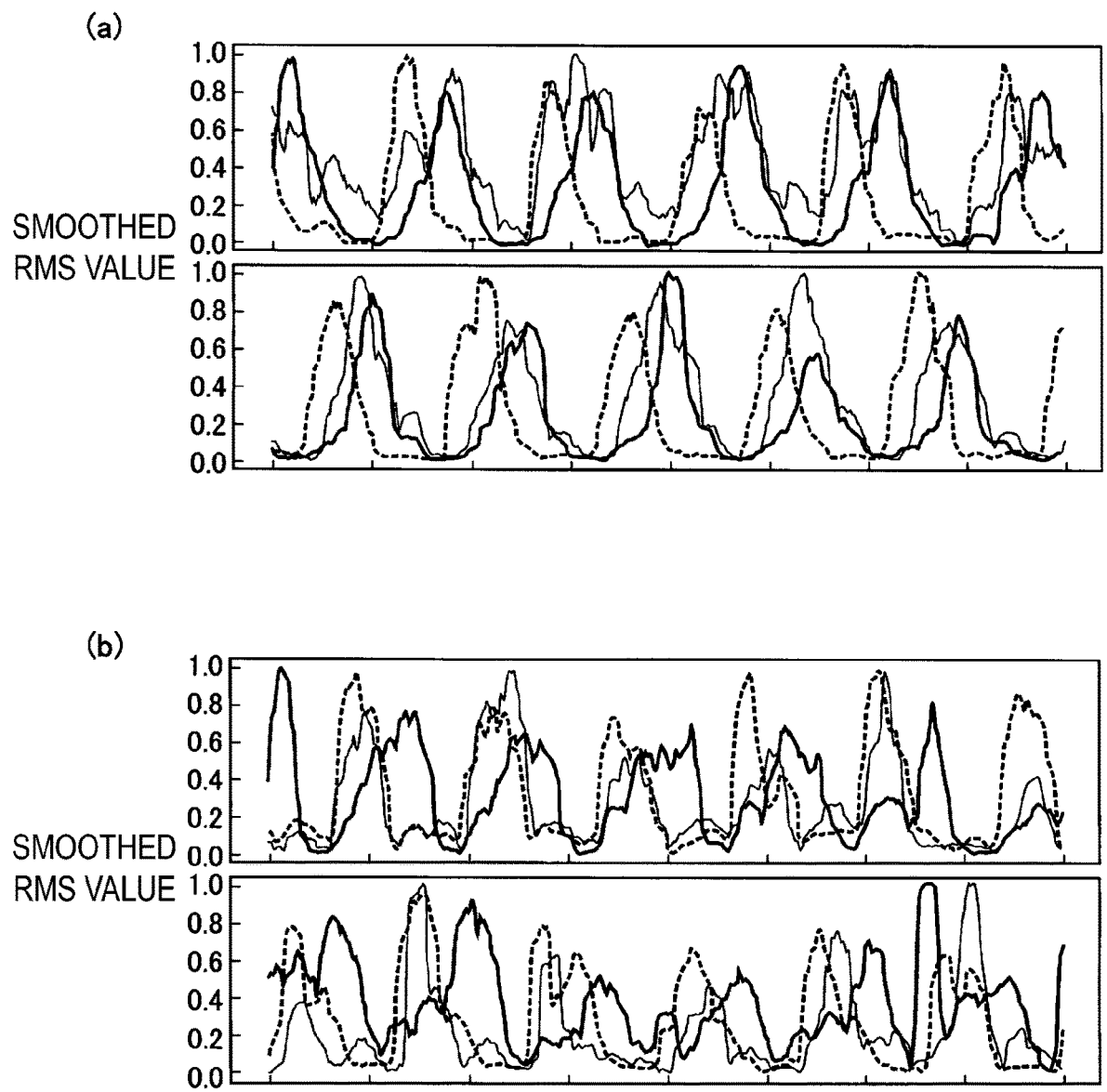
FIG. 10 is a diagram for explaining an example of a normalized RMS value.

FIG. 10 shows the transition of the normalized RMS value in a predetermined section. FIG. 10(*a*) shows data of a professional sportsperson, and FIG. 10(*b*) shows data of an amateur sportsperson. The upper rows of FIGS. 10(*a*) and 10(*b*) each relate to a muscle group of the left leg and the lower rows thereof each relate to a muscle group of the right foot. In FIGS. 10(*a*) and 10(*b*), bold lines each indicate data acquired from the biceps femoris muscle. Solid lines each indicate data acquired from the gluteus maximus muscle. Dashed lines each indicate data acquired from the vastus lateralis muscle.

In each graph of FIG. 10, one peak corresponds to one onset section. The horizontal axis shown in FIG. 10 corresponds to one predetermined section. In the example shown in FIG. 10, one predetermined section includes approximately 5 to 6 onset sections.

In FIG. 10(*a*), similar trends are repeated and there is no significant change in any muscles of the left leg and the right foot. It is seen that the professional sportsperson repeats the repetitive exercise with a high reproducibility.

In FIG. 10(*b*), the graphs each have different trends compared to those in FIG. 10(*a*). It is seen that the amateur sportsperson repeats the repetitive exercise with a low reproducibility. In particular, there is a great variation in the trend of the gluteus maximus muscle, and thus it is considered that the gluteus maximus muscle cannot be stably used.

Figure 11:
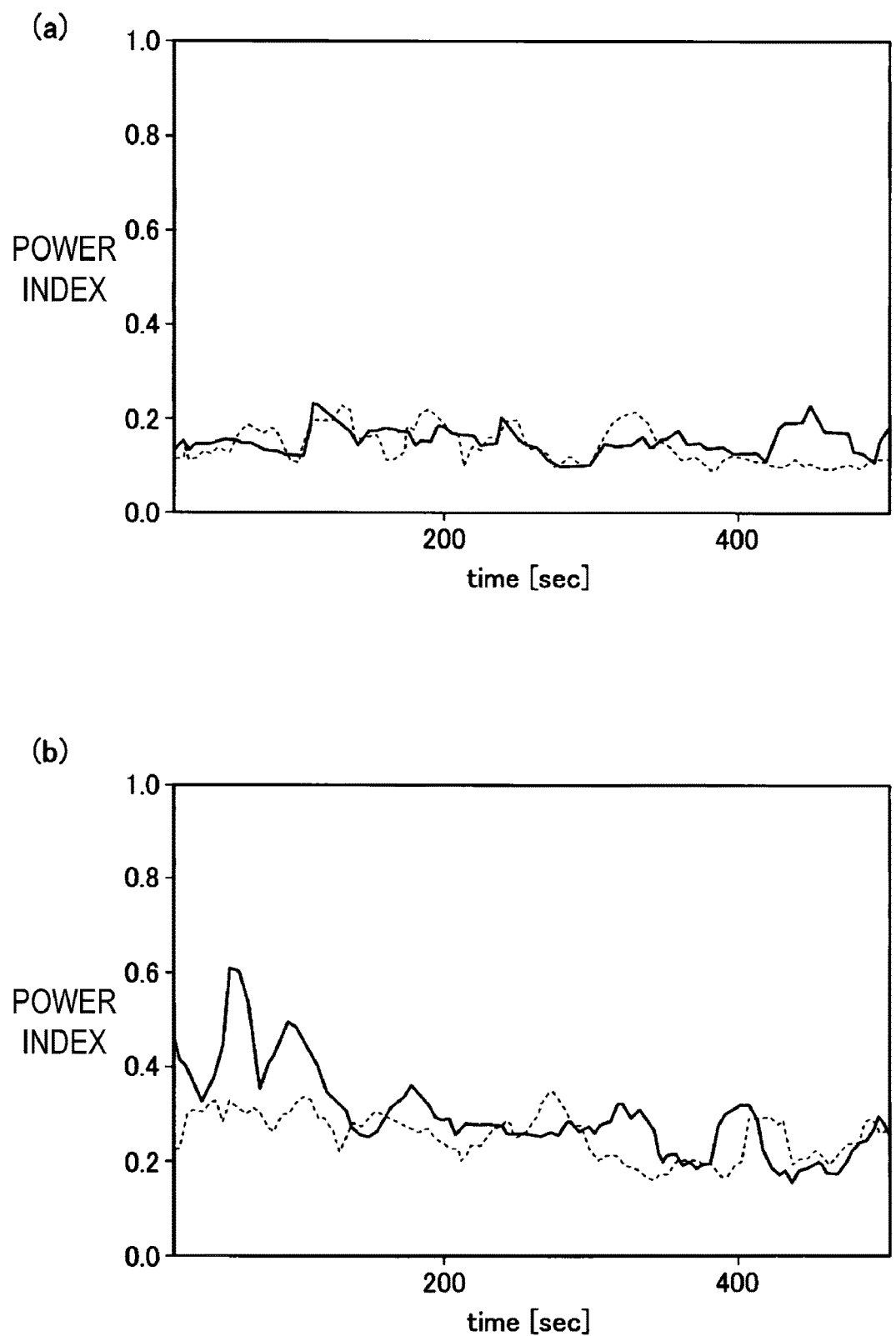
FIG. 11 is a diagram for explaining an example of a power index.

FIG. 11 shows the transition of the power index calculated for each predetermined section. FIG. 11(*a*) shows data of a professional sportsperson, and FIG. 11(*b*) shows data of an amateur sportsperson. FIG. 11 shows transitions of the power indexes for two muscles.

In FIG. 11(*a*), for both the muscles, the power index is low, and thus it is seen that the reproducibility is high. In FIG. 11(*b*), for both the muscles, the power index is high, and thus it is seen that the reproducibility is low. In FIG. 11(*b*), for the gluteus maximus muscle, there is a greater variation than that for the muscle corresponding to the vastus lateralis muscle. It is expected that increasing the reproducibility in the gluteus maximus muscle would increase stability.

Sequence Index Processing Unit

The sequence index processing unit 27 identifies times in which a predetermined condition is satisfied for each muscle in the electromyography data 11 corresponding to the plurality of muscles in the repetitive exercise, identifies a sequence of identifiers of the muscles arranged in the order of the identified times, and calculates a sequence index from the difference in the orders of the identifiers of the muscles for each of the repetitive exercise. Here, the predetermined condition is the timing of any of the start, the peak, and the end of an onset section in which the electromyography is greater than the predetermined value.

The sequence index processing unit 27 outputs a sequence index indicating the reproducibility of the sequence of times in which the electromyography of each muscle satisfies the predetermined condition, in the repetitive exercise. The sequence index processing unit 27 identifies the times of the start, the peak, and the end of the onset section for each of the plurality of muscles. On the basis of the identified times, the sequence index processing unit 27 outputs a sequence index with a high reproducibility when the predetermined conditions corresponding to the times appear in the same sequence. The sequence index is an index indicating the stability of muscle coordination (kinetic chain or kinematic chain).

When calculating the sequence index, the sequence index processing unit 27 converts each RMS value of the RMS data 12 for each muscle to an RMS value normalized in accordance with Equation (1). The sequence index processing unit 27 identifies, for the RMS value of each muscle in the predetermined section, the time at which the onset section has started, the time at which the RMS value has peaked, and the time at which the onset section has ended. Here, the peak is the time at which the normalized RMS value has peaked between the start and the end of the onset section.

For example, for a muscle A and a muscle B, a case will be described in which the sequence index is calculated for predetermined conditions of the peak of the electromyography, and the start and the end of the onset section. With reference to the normalized RMS values, the sequence index processing unit 27 identifies times of the peak of the electromyography, and the start and the end of the onset section for the muscle A. The sequence index processing unit 27 identifies times of the peak of the electromyography, and the start and the end of the onset section for the muscle B.

The sequence index processing unit 27 arranges the predetermined conditions corresponding to the identified times. For example, the sequence index processing unit 27 arranges the predetermined conditions as the start of the onset section for the muscle A, the peak for the muscle A, the start of the onset section for the muscle B, the end of the onset section for the muscle A, the peak for the muscle B, and the end of the onset section for the muscle B, . . . , to identify the sequence of the predetermined conditions.

The sequence index processing unit 27 outputs the variation in the sequence of the identified predetermined conditions as the sequence index for the predetermined section. The sequence index processing unit 27 divides the predetermined section into a plurality of sub-sections, and calculates the variation in the sequences of the predetermined conditions for each of the sub-sections. The sub-section is, for example, a section from the start of an onset section to the start of the next onset section for a muscle.

For example, the sequence index processing unit 27 uses, as the sequence index, the number of rearrangements for unifying the sequences of predetermined conditions in each of the sub-sections. The sequence index processing unit 27 may use the number of rearrangements for obtaining a sequence of a given reference, as the sequence index. When the number of rearrangements is large, specifically, when the timing at which the electromyography of each muscle increases has a low reproducibility, the sequence index increases. When the number of rearrangements is small, specifically, when the timing at which the electromyography of each muscle increases has a high reproducibility, the sequence index decreases.

As another example, the sequence index processing unit 27 may output the sequence index on the basis of only one of the predetermined conditions of the start, the peak, and the end of the onset section. For example, when a case where the peak for the muscle B comes after the peak for the muscle A continues, the sequence index is low and it is thus indicated that the reproducibility is high. When there are a case where the peak for the muscle B comes after the peak for the muscle A and a case where the peak for the muscle A comes after the peak for the muscle B, the sequence index is high and it is thus indicated that the reproducibility is low.

Figure 12:
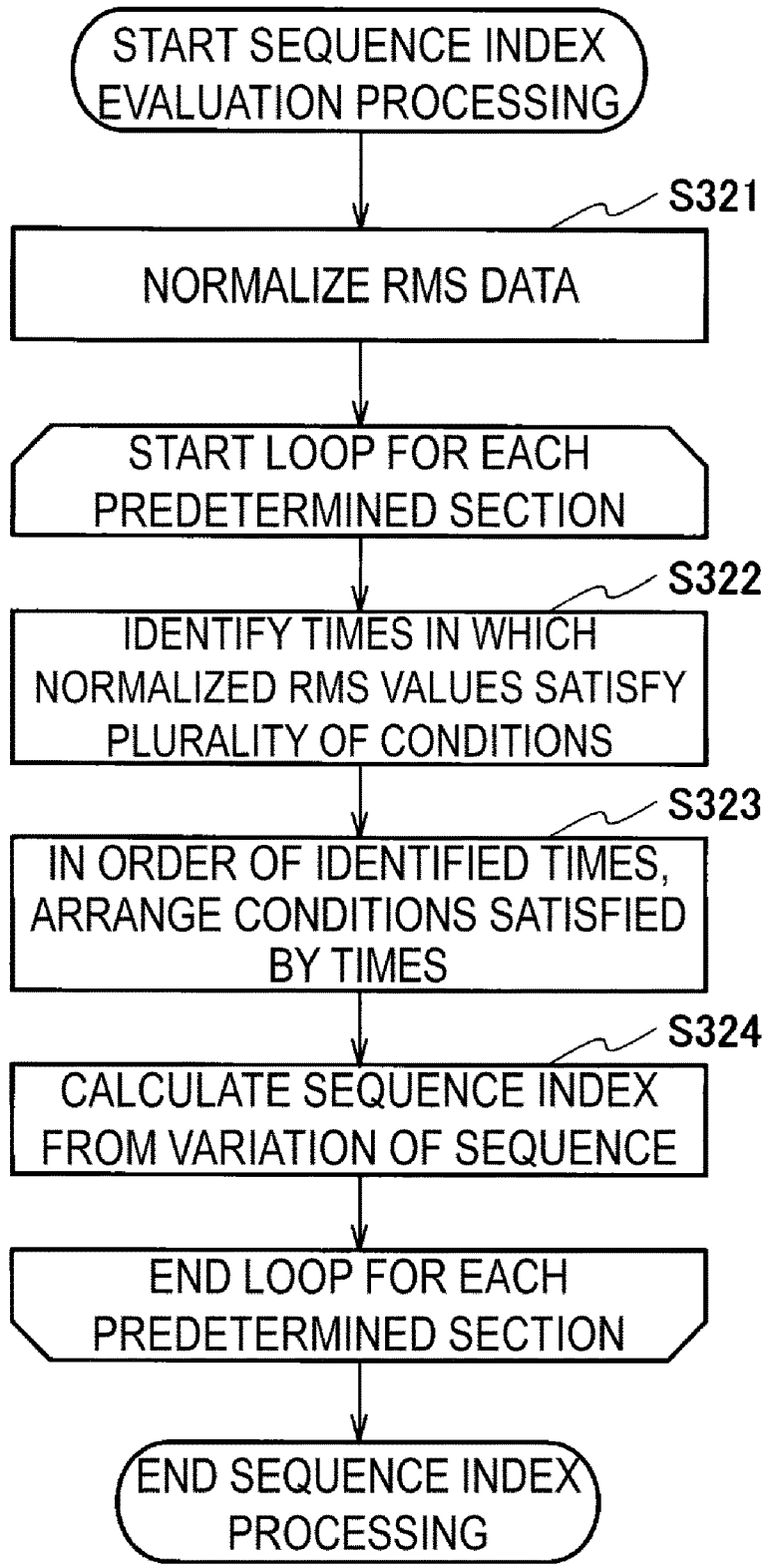
FIG. 12 is a flowchart for explaining sequence index processing by a sequence index processing unit.

Sequence index processing by the sequence index processing unit 27 will be described with reference to FIG. 12.

First, in step S321, the sequence index processing unit 27 normalizes the RMS data 12 of each muscle in accordance with Equation (1).

The sequence index processing unit 27 performs the processing in steps S322 to S324 for the predetermined section. The predetermined section is longer than the interval of the onset section and is a time that includes a plurality of onset sections.

In step S322, the sequence index processing unit 27 identifies times at which the normalized RMS value satisfies each of a plurality of predetermined conditions. In step S323, in the order of the times identified in step S322, the sequence index processing unit 27 arranges predetermined conditions corresponding to the times. In step S324, the sequence index processing unit 27 outputs the sequence index from the variation in the sequence of the predetermined conditions.

When the processing in steps S322 to S324 has ended for each section, the sequence index processing unit 27 ends the processing.

For example, in the example of the professional sportsperson shown in FIG. 10(a), the sequence of the start of the onset section for the vastus lateralis muscle, the start of the onset section for the gluteus maximus muscle, the start of the onset section for the biceps femoris muscle, the peak for the vastus lateralis muscle, the peak for the gluteus maximus muscle, the end of the onset section for the vastus lateralis muscle, the peak for the biceps femoris muscle, the end of the onset section for the biceps femoris muscle, and the end of the onset section for the gluteus maximus muscle is repeated. In the professional sportsperson, the predetermined conditions for the muscles are repeated in a similar sequence and it is thus seen that the muscles can be stably used.

In contrast, in the example of the amateur sportsperson shown in FIG. 10(b), the variation in the sequence is large. In particular, there is a large variation in the sequence for the biceps femoris muscle. It is expected that properly using the biceps femoris muscle would reduce the variation in the sequence of the predetermined conditions, whereby the repetitive exercise can be stable performed.

Time Index Processing Unit

The time index processing unit identifies times, for each muscle, at which a predetermined condition is satisfied in the electromyography data 11 corresponding to a plurality of muscles in the repetitive exercise, and calculates a time index from the difference in the times identified for each of the repetitive exercise and the muscles. Here, the predetermined condition is the timing of any of the start, the peak, and the end of an onset section in which the electromyography is greater than a predetermined value.

The time index processing unit 28 outputs, in the repetitive exercise, a sequence index indicating the reproducibility of the time at which the electromyography of each muscle satisfies the predetermined condition. The time index processing unit 28 identifies times of the start, the peak, and the end of the onset section for each of the plurality of muscles. The time index processing unit 28 outputs a sequence index with a high reproducibility when each identified time appears at the same time in each of sub-sections. The sub-section is, for example, a section from the start of an onset section to the start of the next onset section for a muscle. The time index is an index indicating the stability of muscle coordination (kinetic chain or kinematic chain).

When calculating the time index, the time index processing unit 28 converts each RMS value of the RMS data 12 for each muscle to an RMS value normalized in accordance with Equation (1). The time index processing unit 28 identifies, for the RMS value for each muscle in the predetermined section, the time at which the onset section has started, the time at which the RMS value has peaked, and the time at which the onset section has ended. Here, the peak is the time at which the normalized RMS value has peaked between the start and the end of the onset section.

For example, a case will be described in which the sequence index is calculated for predetermined conditions of the peak of the electromyography, and the start and the end of the onset section for a muscle A and a muscle B. With reference to the normalized RMS value, the time index processing unit 28 identifies times of the peak, the start, and the end of the onset section of the electromyography for the muscle A. The time index processing unit 28 identifies times of the peak, the start, and the end of the onset section of the electromyography for the muscle B.

The time index processing unit 28 normalizes the identified times to times in the sub-sections. The normalized times each take a value from 0 to 1 with the time of the sub-section being 1. When the times at which the predetermined condition is satisfied for each muscle are converted to the normalized times in the sub-section, it is possible to evaluate whether the predetermined condition is satisfied at the same time even in a case where the lengths of the sub-sections differ.

The time index processing unit 28 uses the variance of the normalized times as the time index. When five sub-sections are included in the predetermined section, there are generally five normalized times at which one predetermined condition is satisfied. The time index is calculated from the variance of these five normalized times. When the variance is large, specifically, when the reproducibility at which the predetermined condition is satisfied at the same time is low, the time index increases. When the variance is small, specifically, when the reproducibility at which the predetermined condition is satisfied at the same time is high, the time index decreases.

When calculating the time index with a plurality of predetermined conditions, for each of the predetermined conditions, the time index processing unit 28 calculates the variance of the normalized times at which the predetermined condition is satisfied. The time index processing unit 28 calculates the time index from an average of the variances calculated for the predetermined conditions and the like.

Figure 13:
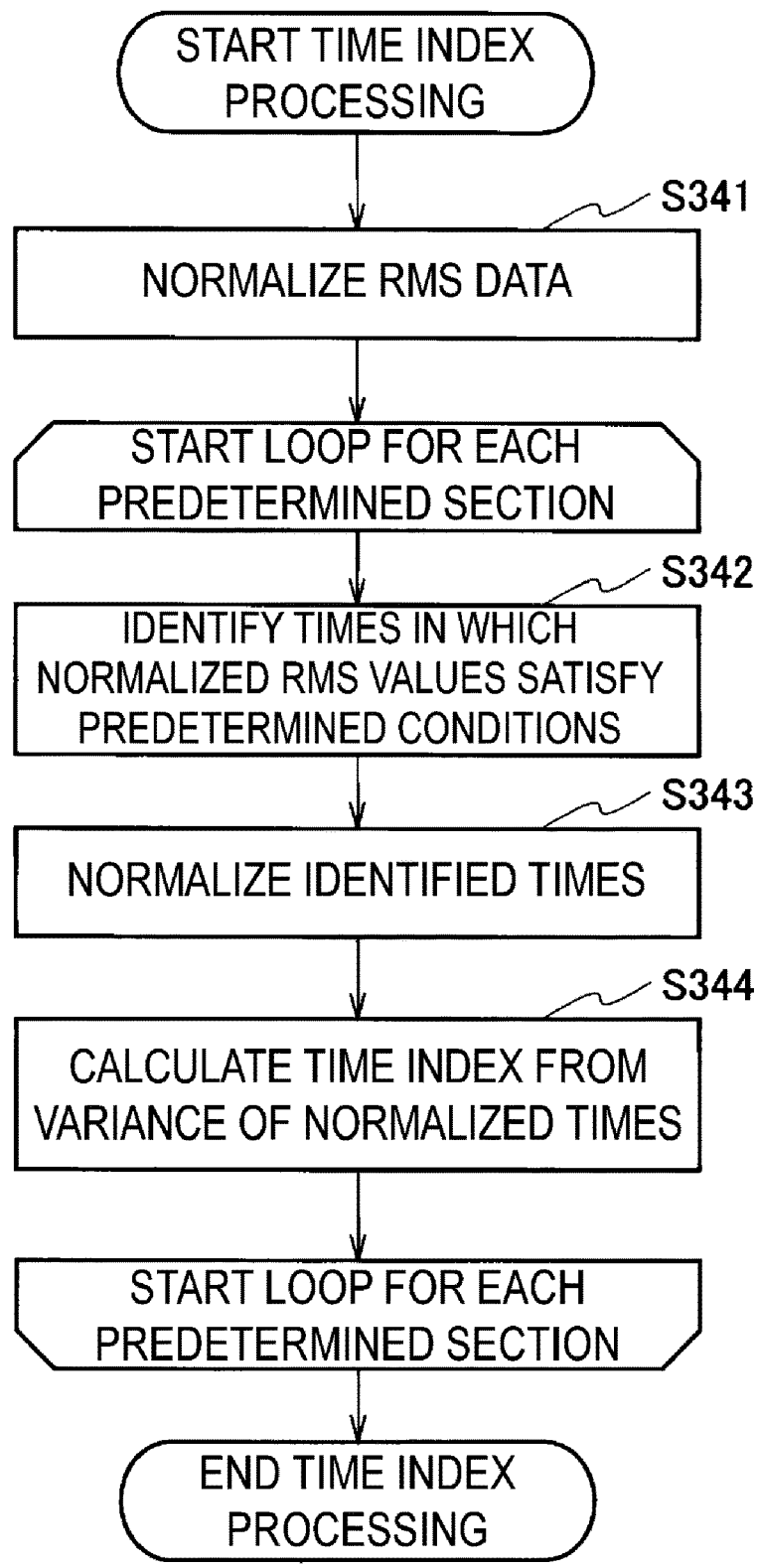
FIG. 13 is a flowchart for explaining time index processing by a time index processing unit.

Sequence index processing by the time index processing unit 28 will be described with reference to FIG. 13.

First, in step S341, the time index processing unit 28 normalizes the RMS data 12 of each muscle in accordance with Equation (1).

The time index processing unit 28 performs the processing in steps S342 to S344 for a predetermined section. The predetermined section is longer than the interval of the onset section and is a time that includes a plurality of onset sections.

In step S342, the time index processing unit 28 identifies times at which the normalized RMS value satisfies a plurality of predetermined conditions. In step S343, the time index processing unit 28 normalizes the times identified in step S322. In step S324, the time index processing unit 28 outputs a time index from the variation of the normalized times.

When the processing in steps S342 to S344 ends for each section, the time index processing unit 28 ends the processing.

Reproducibility Index Output Unit

The reproducibility index output unit 29 calculates and outputs a reproducibility index. The reproducibility index is the power index, the sequence index, or the time index. Alternatively, the reproducibility index is an index in which two or more indexes of the power index, the sequence index, and the time index are integrated. The reproducibility index is calculated by multiplying each of the indexes to be integrated by a predetermined weight and adding together the multiplied indexes. The reproducibility index output unit 29 stores the reproducibility index for each time in the reproducibility index data.

The reproducibility index output unit 29 may display the reproducibility index at each time in a time-series graph. The reproducibility index output unit 29 may output a result obtained by converting the reproducibility index by means of a predetermined conversion, rather than the reproducibility index itself. The reproducibility index output unit 29 may represent the reproducibility index by the number of points out of 100 points such that the reproducibility index "0" is represented by 100 points. The reproducibility index output unit 29 may represent the reproducibility index by a graded scale such as "Good", "Average", and "Bad" such that the reproducibility index 0 is represented by "Good".

Figure 14:
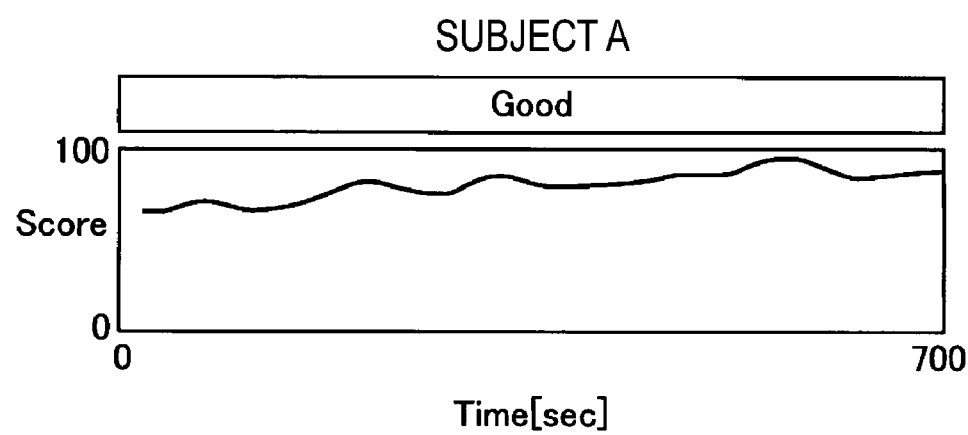
FIG. 14 is an example of output from a reproducibility index output unit.
Figure 14:
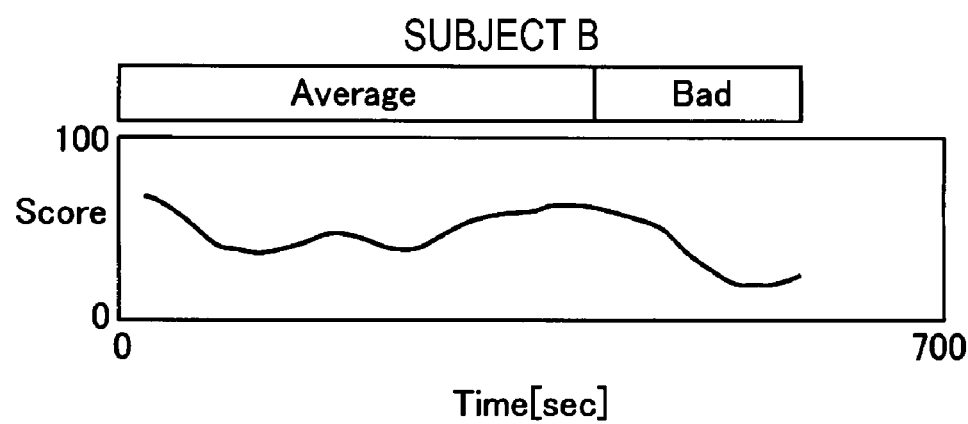
Figure 15:
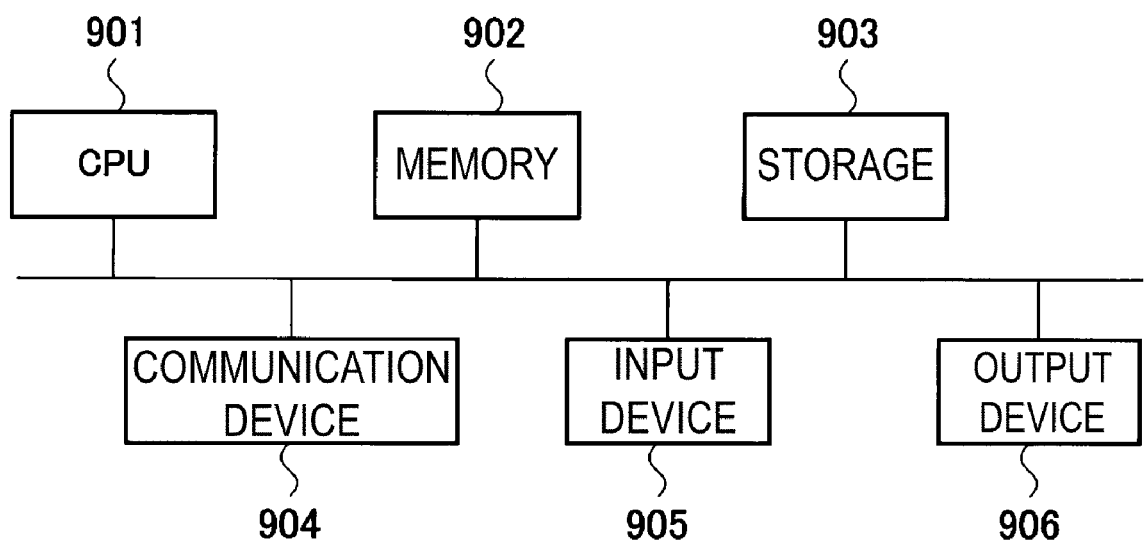
FIG. 15 is a diagram for explaining a hardware configuration of a computer.

An example of an evaluation output by the reproducibility index output unit 29 will be described with reference to FIG. 14. FIG. 14 shows a score at each time calculated from the reproducibility index. When the reproducibility index is closer to 0, the score approaches 100, and when the reproducibility index is higher, the score approaches 0. Furthermore, in FIG. 14, three evaluations of "Good", "Average", and "Bad" are associated in accordance with the transition of the score. FIG. 10(*a*) shows data of a professional sportsperson and FIG. 8(*b*) shows data of an amateur sportsperson.

In FIG. 10(*a*), a state in which the score is close to 100 is maintained and overall an evaluation of "Good" is given. In FIG. 10(*b*), the score is low compared to that in FIG. 10(*a*), and an evaluation of "Average" is initially given, but an evaluation of "Bad" is given in the later half in which the score further lowers.

The electromyography processing apparatus 1 according to the embodiment can output the reproducibility index that evaluates the reproducibility of the movement of each muscle in the repetitive exercise on the basis of the trend of the electromyography measured from the muscle.

Furthermore, the electromyography processing apparatus 1 can notify the exerciser of a low proficiency of the repetitive exercise, or an instability due to a change in form and the like, by means of the reproducibility index. The electromyography processing apparatus 1 can evaluate the learning of efficient and natural motions and the adaptation to a new form.

As the electromyography processing apparatus 1 according to the present embodiment described above, for example, a general-purpose computer system including a central processing unit (CPU; processor) 901, a memory 902, a storage 903 (hard disk drive (HDD) or a solid state drive (SSD)), a communication device 904, an input device 905, and an output device 906 is used. The CPU 901 is the processing device 20. The memory 902 and the storage 903 are the storage device 10. In the computer system, the CPU 901 executes a predetermined program loaded into the memory 902 to implement each function of the electromyography processing apparatus 1.

Note that the electromyography processing apparatus 1 may be implemented by one computer or may be implemented by a plurality of computers. The electromyography processing apparatus 1 may be a virtual machine implemented on a computer.

The program for the electromyography processing apparatus 1 may be stored in a computer-readable recording medium such as an HDD, an SSD, a universal serial bus (USB) memory, a compact disc (CD), or a digital versatile disc (DVD), or may be distributed through a network.

The present disclosure is not limited to the embodiment, and various modifications can be made within the scope of the gist of the present disclosure.

REFERENCE SIGNS LIST

1 Electromyography processing apparatus
11 Electromyography data
12 RMS data
13 Onset data
14 Reproducibility index data
20 Processing device
21 Electromyography acquiring unit
22 Preprocessing unit
23 Onset detection unit
24 Threshold determination unit
25 Evaluation unit
26 Power index processing unit
27 Sequence index processing unit
28 Time index processing unit
29 Reproducibility index output unit
30 Input/output interface
901 CPU
902 Memory
903 Storage
904 Communication device
905 Input device
906 Output device

The invention claimed is:

1. An electromyography processing apparatus comprising:
   an electromyography acquiring unit comprising one or more hardware processors and configured to generate electromyography data indicating a time course of an electromyography acquired from an electrode set on a predetermined muscle of an exerciser performing repetitive exercises; and
   an evaluation unit comprising the one or more hardware processors and configured to calculate and output a reproducibility index indicating a reproducibility of each of the repetitive exercises from a reproducibility of a transition of the electromyography in each of the repetitive exercises, wherein the reproducibility index is a power index, and the evaluation unit is configured to calculate the power index from a variance of integrated values of the electromyography for every predetermined time.

2. The electromyography processing apparatus according to claim 1, wherein
   the evaluation unit configured to calculate, as the power index, a coefficient of variation obtained by dividing a standard deviation of the integrated values of the electromyography for every predetermined time by an average of the integrated values.

3. The electromyography processing apparatus according to claim 1, wherein
   the reproducibility index is a sequence index,
   the electromyography acquiring unit configured to generate pieces of electromyography data indicating time courses of electromyographies corresponding to a plurality of muscles, and
   the evaluation unit configured to identify times at which a predetermined condition is satisfied, for each of the plurality of muscles in the pieces of electromyography data corresponding to the plurality of muscles in the corresponding repetitive exercises, identify a sequence of identifiers of the plurality of muscles arranged in order of the times that are identified, and calculate the sequence index from a difference in the sequence of the identifiers of the plurality of muscles for each of the repetitive exercises.

4. The electromyography processing apparatus according to claim 3, wherein
   the predetermined condition is a timing of any of a start, a peak, and an end of an onset section in which each of the electromyographies is greater than a predetermined value.

5. The electromyography processing apparatus according to claim 1, wherein
   the reproducibility index is a time index,
   the electromyography acquiring unit configured to generate pieces of electromyography data indicating time courses of electromyographies corresponding to a plurality of muscles, and
   the evaluation unit configured to identify times at which a predetermined condition is satisfied, for each of the plurality of muscles in the pieces of electromyography data corresponding to the plurality of muscles in the corresponding repetitive exercises, and calculate the time index from a difference in the times identified for each of the repetitive exercises and for each of the plurality of muscles.

6. An electromyography processing method comprising:
   generating, by a computer, electromyography data indicating a time course of an electromyography acquired from an electrode set on a predetermined muscle of an exerciser performing repetitive exercises; and
   calculating and outputting, by the computer, a reproducibility index indicating a reproducibility of each of the repetitive exercises from a reproducibility of a transition of the electromyography in each of the repetitive exercises, wherein the reproducibility index is a power index, and the power index is calculated from a variance of integrated values of the electromyography for every predetermined time.

7. A computer-readable recording medium storing an electromyography processing program executable to cause one or more computers to perform operations, the operations comprising:
   generating, by a computer, electromyography data indicating a time course of an electromyography acquired from an electrode set on a predetermined muscle of an exerciser performing repetitive exercises; and
   calculating and outputting, by the computer, a reproducibility index indicating a reproducibility of each of the repetitive exercises from a reproducibility of a transition of the electromyography in each of the repetitive exercises, wherein the reproducibility index is a power index, and the power index is calculated from a variance of integrated values of the electromyography for every predetermined time.

* * * * *